US00PP27566P2

(12) United States Plant Patent
Westhoff

(10) Patent No.: US PP27,566 P2
(45) Date of Patent: Jan. 17, 2017

(54) ***CALIBRACHOA* PLANT NAMED 'WESCACHAM'**

(50) Latin Name: ***Calibrachoa* sp.**
Varietal Denomination: Wescacham

(71) Applicant: Heinrich Westhoff, Sudlohn (DE)

(72) Inventor: Heinrich Westhoff, Sudlohn (DE)

(73) Assignee: Gartenbau und Spezialkulturen Westhoff GbR, Sudlohn (DE)

( * ) Notice: Subject to any disclaimer, the term of this patent is extended or adjusted under 35 U.S.C. 154(b) by 110 days.

(21) Appl. No.: 14/544,738

(22) Filed: Feb. 10, 2015

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Keith Robinson
(74) *Attorney, Agent, or Firm* — C. A. Whealy

(57) ABSTRACT

A new and distinct cultivar of *Calibrachoa* plant named 'Wescacham', characterized by its compact, semi-upright and mounding growth habit; moderately vigorous growth habit; freely branching habit; freely flowering habit; medium-sized flowers that are pale creamy yellow and dark pink in color; the varying amount of pale creamy yellow and dark pink colors is dependent on environment and developmental stage of the flower; and good garden performance.

3 Drawing Sheets

Botanical designation: *Calibrachoa* sp.
Cultivar denomination: 'WESCACHAM'.

BACKGROUND OF THE INVENTION

The present invention relates to a new and distinct cultivar of *Calibrachoa* plant, botanically known as *Calibrachoa* sp. and hereinafter referred to by the name 'Wescacham'.

The new *Calibrachoa* plant is a product of a planned breeding program conducted by the Inventor in Südlohn, Germany. The objective of the breeding program is to create new compact *Calibrachoa* plants with uniform plant habit and numerous attractive and uniquely-colored flowers.

The new *Calibrachoa* plant originated from a cross-pollination made by the Inventor in June, 2011 in Südlohn, Germany of a proprietary selection of *Calibrachoa* sp. identified as code number Ca 11-50, not patented, as the female, or seed, parent with a proprietary selection of *Calibrachoa* sp. identified as code number Ca 11-03, not patented, as the male, or pollen, parent. The new *Calibrachoa* plant was discovered and selected by the Inventor as a single flowering plant within the progeny of the stated cross-pollination in a controlled environment in Südlohn, Germany in May, 2012.

Asexual reproduction of the new *Calibrachoa* plant by vegetative cuttings in a controlled greenhouse environment in Südlohn, Germany since June, 2012 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Wescacham'. These characteristics in combination distinguish 'Wescacham' as a new and distinct *Calibrachoa* plant:

1. Compact, semi-upright and mounding growth habit.
2. Moderately vigorous growth habit.
3. Freely branching habit.
4. Freely flowering habit.
5. Medium-sized flowers that are pale creamy yellow and dark pink in color; the varying amount of pale creamy yellow and dark pink colors is dependent on environment and developmental stage of the flower.
6. Good garden performance.

Plants of the new *Calibrachoa* can be compared to plants of the female parent selection. Plants of the new *Calibrachoa* differ primarily from plants of the female parent selection in the following characteristics:

1. Plants of the new *Calibrachoa* are not as upright as plants of the female parent selection.
2. Plants of the new *Calibrachoa* have smaller flower buds and flowers than plants of the female parent selection.
3. Plants of the new *Calibrachoa* and the female parent selection differ in flower color as plants of the female parent selection have light yellow-colored flowers.

Plants of the new *Calibrachoa* can be compared to plants of the male parent selection. Plants of the new *Calibrachoa* differ primarily from plants of the male parent selection in the following characteristics:

1. Plants of the new *Calibrachoa* are not as trailing as plants of the male parent selection.
2. Plants of the new *Calibrachoa* have smaller leaves than plants of the male parent selection.
3. Plants of the new *Calibrachoa* flower later than plants of the male parent selection.
4. Plants of the new *Calibrachoa* and the male parent selection differ in flower color as plants of the male parent selection have pink-colored flowers.

Plants of the new *Calibrachoa* can be compared to plants of the *Calibrachoa* sp. 'Wescasun', disclosed in U.S. Plant Pat. No. 12,756. In side-by-side comparisons conducted in Südlohn, Germany, plants of the new *Calibrachoa* differed from plants of 'Wescasun' in the following characteristics:

1. Plants of the new *Calibrachoa* were more compact than plants of 'Wescasun'.
2. Plants of the new *Calibrachoa* were more upright than and not as hanging as plants of 'Wescasun'.
3. Plants of the new *Calibrachoa* were not as vigorous as plants of 'Wescasun'.
4. Plants of the new *Calibrachoa* had shorter leaves than plants of 'Wescasun'.
5. Plants of the new *Calibrachoa* had smaller flower buds and flowers than plants of 'Wescasun'.
6. Plants of the new *Calibrachoa* and 'Wescasun' differed in flower color as plants of 'Wescasun' had intense yellow-colored flowers.

Plants of the new *Calibrachoa* can also be compared to plants of the *Calibrachoa* sp. 'Celebration Lemon Ice', not patented. In side-by-side comparisons conducted in Südlohn, Germany, plants of the new *Calibrachoa* differed from plants of 'Celebration Lemon Ice' in the following characteristics:

1. Plants of the new *Calibrachoa* had smaller flowers than plants of 'Celebration Lemon Ice'.
2. Plants of the new *Calibrachoa* and 'Celebration Lemon Ice' differed in flower color as plants of 'Celebration Lemon Ice' had light yellow-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet comprises a side perspective view of a typical flowering plant of 'Wescacham' grown in a container.

The photograph on the second sheet is a close-up view of typical flowers of 'Wescacham' showing the flower color variations of 'Wescacham'.

The photograph on the third sheet is a close-up view of a typical flowering plant of 'Wescacham'.

DETAILED BOTANICAL DESCRIPTION

The aforementioned photographs and following observations, measurements and values describe plants grown in 12-cm containers in Südlohn, Germany, under typical commercial cultural practices during the spring in a glass-covered greenhouse with day temperatures ranging from 20° C. to 25° C., night temperatures ranging from 16° C. to 18° C. and light levels ranging from 3 to 50 klux. Plants were pinched two times and were 15 weeks old when the photograph and description were taken. In the following description, color references are made to The Royal Horticultural Society Colour Chart, 2001 Edition, except where general terms of ordinary dictionary significance are used.

Botanical classification: *Calibrachoa* sp. 'Wescacham'.

Parentage:

*Female, or seed, parent*.—Proprietary selection of *Calibrachoa* sp. identified as code number Ca 11-50, not patented.

*Male, or pollen, parent*.—Proprietary selection of *Calibrachoa* sp. identified as code number Ca 11-03, not patented.

Propagation:

*Type*.—By vegetative tip cuttings.

*Time to initiate roots, summer*.—About 21 to 24 days at temperatures about 18° C. to 20° C.

*Time to initiate roots, winter*.—About 24 to 28 days at temperatures about 18° C. to 20° C.

*Time to produce a rooted young plant, summer*.—About four to five weeks at temperatures about 18° C. to 20° C.

*Time to produce a rooted young plant, winter*.—About five to six weeks at temperatures about 18° C. to 20° C.

*Root description*.—Fibrous, medium in thickness; color, close to 199D and 156D.

*Rooting habit*.—Freely branching; moderately dense to dense.

Plant description:

*Plant and growth habit*.—Compact, semi-upright to mounding growth habit; freely branching habit with lateral branches potentially developing at every node; moderately vigorous growth habit.

*Plant height*.—About 14 cm to 17 cm.

*Plant diameter*.—About 33 cm.

Lateral branch description:

*Length*.—About 5 cm to 8 cm.

*Diameter*.—About 1.2 mm.

*Internode length*.—About 1 cm to 1.8 cm.

*Strength*.—Strong; flexible.

*Aspect*.—Initially upright to outwardly spreading.

*Texture*.—Densely pubescent.

*Color*.—Close to 144A.

Leaf description:

*Arrangement*.—Alternate, simple; sessile.

*Length*.—About 2.6 cm to 3.3 cm.

*Width*.—About 1.2 cm to 1.7 cm.

*Shape*.—Broadly ovate.

*Apex*.—Acute.

*Base*.—Attenuate.

*Margin*.—Entire.

*Texture, upper and lower surfaces*.—Sparsely pubescent.

*Venation pattern*.—Pinnate; arcuate.

*Color*.—Developing leaves, upper surface: Close to 146A. Developing leaves, lower surface: Close to 146B. Fully expanded leaves, upper surface: Close to 147A; venation, close to 147B. Fully expanded leaves, lower surface: Close to 147B; venation, close to 147C.

Flower description:

*Flower arrangement and habit*.—Single salverform flowers arising from leaf axils; freely flowering habit with numerous flowers developing per plant; flowers face mostly outwardly.

*Fragrance*.—None detected.

*Natural flowering season*.—Plants flower continuously from spring until the end of autumn in Germany.

*Flower longevity*.—Individual flowers last about a week on the plant; flowers not persistent.

*Flower diameter*.—About 2.8 cm to 3.1 cm.

*Flower length* (*height*).—About 2.2 cm to 2.4 cm.

*Flower buds*.—Shape: Oblong. Length: About 1.5 cm to 1.7 cm. Diameter: About 5 mm. Color: Close to 1B.

*Corolla*.—Arrangement: Five petals fused at the base and opening into a flared trumpet. Petal length from throat: About 1.5 cm. Petal lobe width: About 1.4 cm. Petal shape: Roughly semi-circular. Petal apex: Obtuse. Petal margin: Entire. Petal texture, upper and lower surfaces: Smooth, glabrous; dull. Color: When opening and fully opened, upper surface: Close to 1C and N74A to N74B; the amount of pale creamy yellow and dark pink colors varies with environment and developmental stage of the flower; throat, close to N84A; color becoming closer to N74A to N74C with development. When opening and fully opened, lower surface: Close to 1D and N74B to N74C; the amount of pale creamy yellow and dark pink colors varies with environment and developmental stage of the flower; color becoming closer to N74C to N74D with development.

*Calyx*.—Arrangement: One star-shaped calyx tube with five sepals fused at the base per flower. Sepal length: About 1.3 cm to 1.8 cm. Sepal width: About 4 mm to 5 mm. Sepal shape: Lanceolate. Sepal apex: Obtuse. Sepal margin: Entire. Sepal texture, upper and lower surfaces: Smooth, glabrous. Color, upper surface: Close to 147A. Color, lower surface: Close to 147B.

*Peduncles*.—Length: About 2.2 cm to 2.9 cm. Diameter: About 1 mm. Strength: Moderately strong; flexible. Texture: Pubescent. Color: Close to 144B.

*Reproductive organs*.—Stamens: Quantity: About five per flower. Filament length: About 3.5 mm to 6 mm. Filament color: Close to 144D. Anther shape: Ovate, four-parted. Anther length: About 1 mm to 1.5 mm. Anther color: Close to 9A. Pollen amount: Moderate. Pollen color: Close to 9A. Pistils: Quantity: One per flower. Pistil length: About 9 mm. Style length: About 7 mm. Style color: Close to 144C. Stigma shape: Ovate; two-parted. Stigma color: Close to 144B. Ovary color: Close to 144B. Seeds: Length: About 8 mm to 10 mm. Diameter: About 8 mm to 10 mm. Color: Close to N187A.

Garden performance: Plants of the new *Calibrachoa* have been observed to have good garden performance and tolerate wind, rain and temperatures ranging from about 16° C. to about 28° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'Wescacham' as illustrated and described.

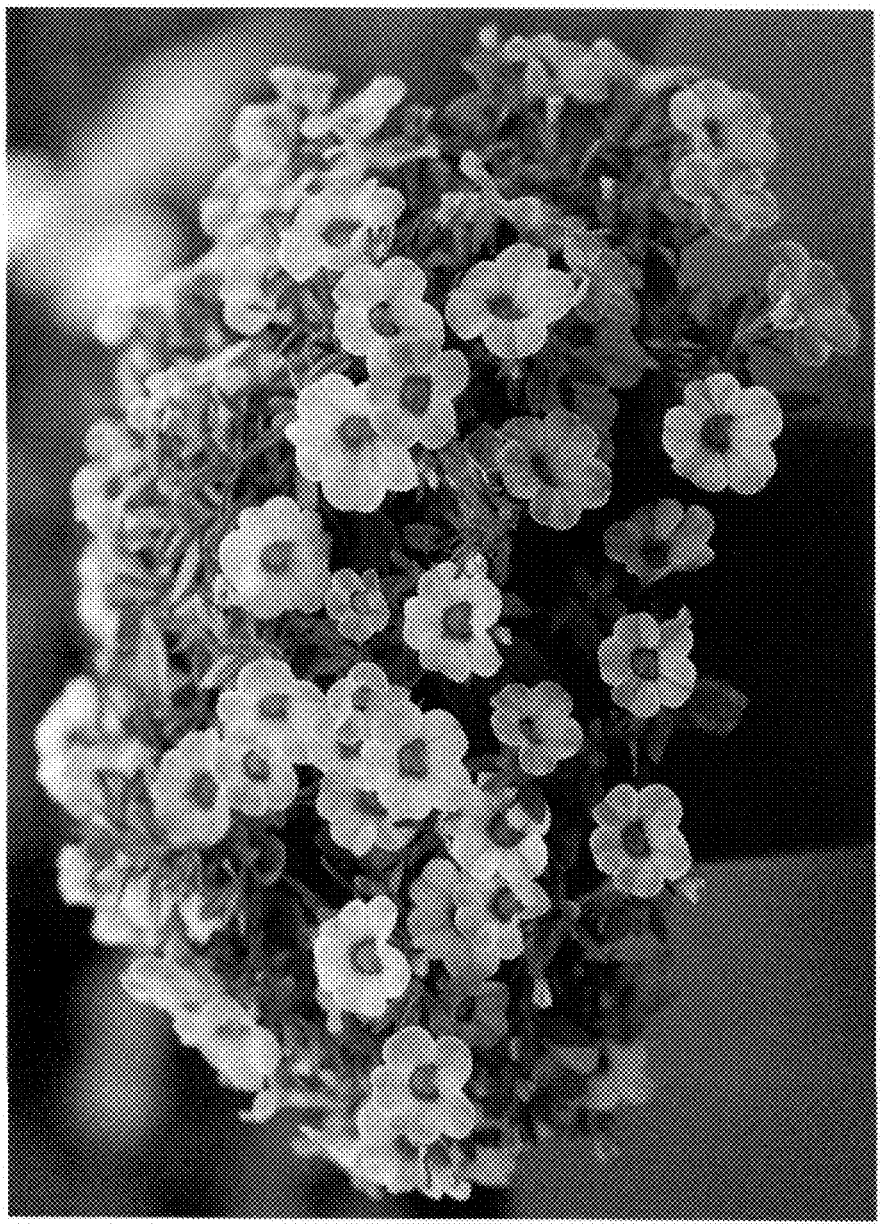

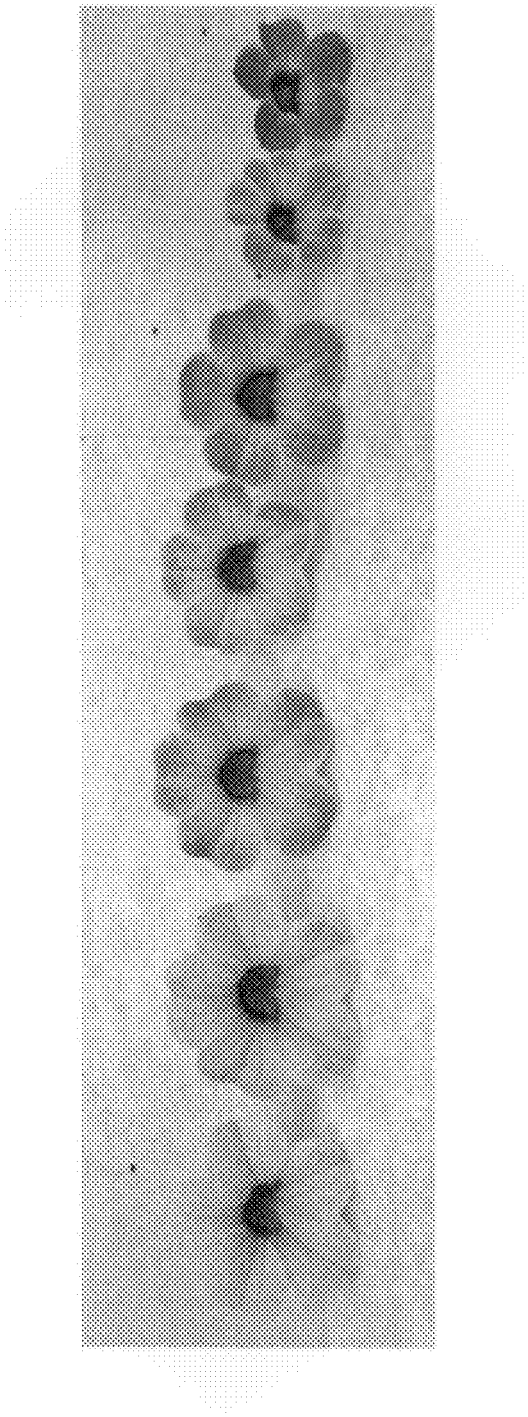

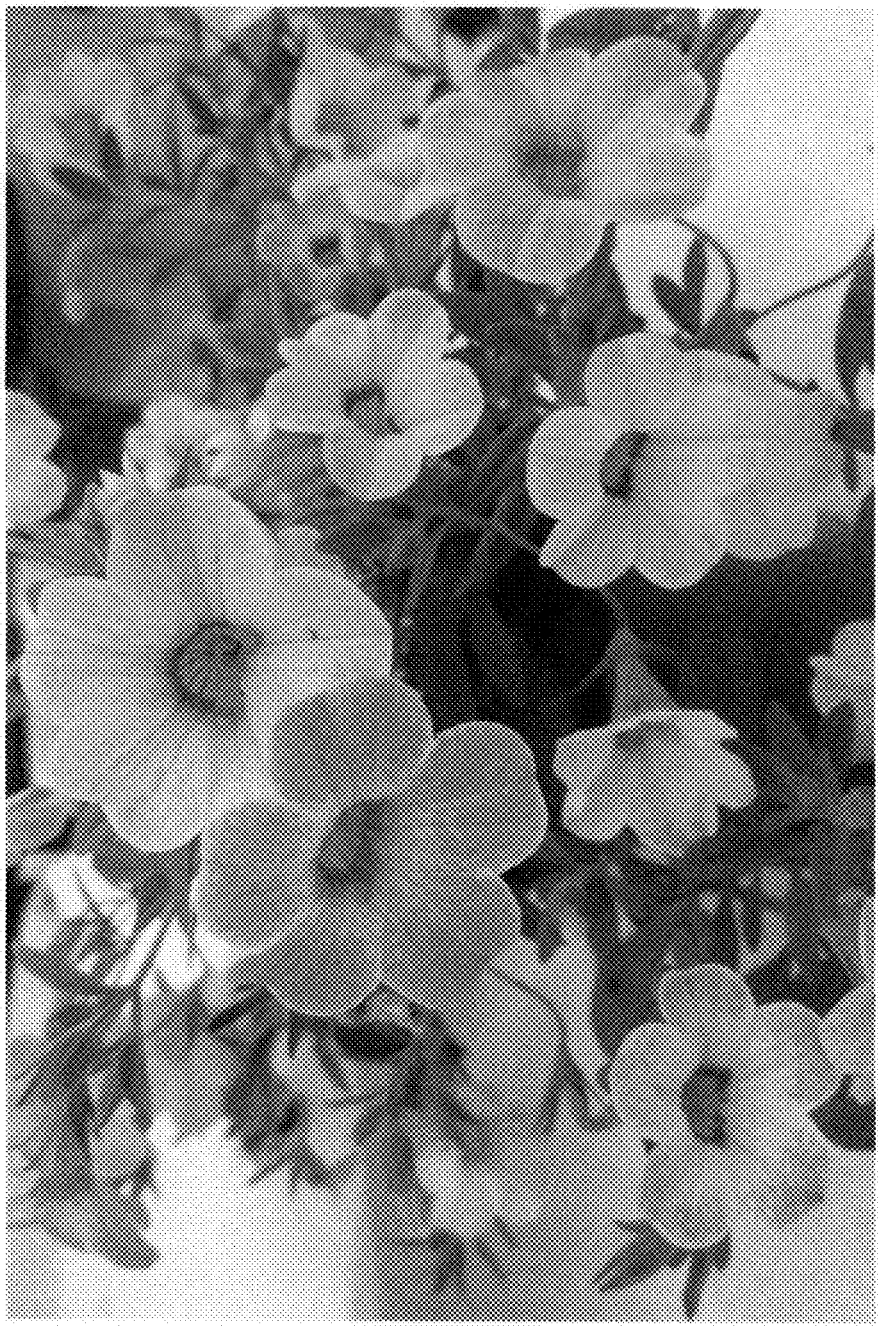

* * * * *